United States Patent
Muramoto et al.

(10) Patent No.: US 9,902,968 B2
(45) Date of Patent: Feb. 27, 2018

(54) METHOD FOR INCREASING PLANT BIOMASS USING AN EXOGENOUS GENE ENCODING A THERMOPHILIC RESTRICTION ENZYME

(71) Applicants: KABUSHIKI KAISHA TOYOTA CHUO KENKYUSHO, Nagakute-shi, Aichi-ken (JP); THE UNIVERSITY OF TOKYO, Tokyo (JP)

(72) Inventors: Nobuhiko Muramoto, Gifu (JP); Hiroki Sugimoto, Nagakute (JP); Norihiro Mitsukawa, Miyoshi (JP); Kunihiro Ohta, Tokyo (JP); Kazuto Kugou, Tokyo (JP)

(73) Assignees: KABUSHIKI KAISHA TOYOTA CHUO KENKYUSHO, Nagakute (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/203,090

(22) Filed: Mar. 10, 2014

(65) Prior Publication Data
US 2014/0273126 A1    Sep. 18, 2014

(30) Foreign Application Priority Data
Mar. 12, 2013    (JP) ................................ 2013-049689

(51) Int. Cl.
*C12N 15/82*    (2006.01)
*C12N 9/22*    (2006.01)

(52) U.S. Cl.
CPC .......... *C12N 15/8261* (2013.01); *C12N 9/22* (2013.01); *C12Y 301/21004* (2013.01)

(58) Field of Classification Search
None
See application file for complete search history.

(56) References Cited

U.S. PATENT DOCUMENTS

| | | | |
|---|---|---|---|
| 6,770,800 B2 | 8/2004 | Gordon-Kamm et al. | |
| 7,825,295 B2 | 11/2010 | Inze et al. | |
| 8,865,969 B2* | 10/2014 | Kondo | C12N 15/8213 435/469 |
| 2008/0076159 A1* | 3/2008 | Baez-Vasquez et al. | 435/72 |
| 2008/0166809 A1 | 7/2008 | Ohta et al. | |
| 2010/0199387 A1 | 8/2010 | Yoshizumi et al. | |
| 2011/0277189 A1* | 11/2011 | Kondo | C12N 15/8213 800/293 |
| 2013/0007911 A1* | 1/2013 | Stewart, Jr. | C12N 15/827 800/278 |

FOREIGN PATENT DOCUMENTS

| | | |
|---|---|---|
| JP | 2006-141322 A | 6/2006 |
| JP | 2011-160798 A | 8/2011 |
| JP | 2012-044883 A | 3/2012 |
| WO | WO 2008/120410 A1 | 10/2008 |
| WO | 2010/073697 A1 | 7/2010 |

OTHER PUBLICATIONS

Adachia et al, PNAS (2011) vol. 108 pp. 10004-10009).*
Barany et al, Gene (1992) vol. 112 pp. 3-12.*
Bleuyard et al, DNA Repair (2006) vol. 5 pp. 1-12.*
Guo et al (2004), Proc. Natl. Acad. Sci. USA vol. 101 pp. 9205-9210.*
Ngo et al. In the Protein Folding Problem and Tertiary Structure Prediction, 1994, Merz et al. (ed.), Birkhauser, Boston, MA, pp. 491-495.*
Acquaah, Principles of Plant Genetics and Breeding (2007) pp. 164-180, Blackwell Publishing, 350 Main Street, Malden, MA 02148-5020, USA.*
Adachi et al, PNAS (2011) vol. 108 pp. 10004-10009.*
Veylder et al., "Control of Proliferation, Endoreduplication and Differentiation by the *Arabidopsis* E2Fa-Dpa Transcription Factor," *The EMBO Journal*, 2002, vol. 21, No. 6, pp. 1360-1368.
Ishida et al., "SUMO E3 Ligase High PLOIDY2 Regulates Endocycle Onset and Meristem Maintenance in *Arabidopsis*," *The Plant Cell*, Aug. 2009, vol. 21, pp. 2284-2297.
Sugimoto-Shirasu et al., "RHL1 is an Essential Component of the Plant DNA Topoisomerase VI Complex and is Required for Ploidy-Dependent Cell Growth," *PNAS*, Dec. 2005, vol. 102, No. 51, pp. 18736-18741.
Adachi et al., "Programmed Induction of Endoreduplication by DNA Double-Strand Breaks in *Arabidopsis*," *PNAS*, Jun. 2011, vol. 108, No. 24, pp. 10004-10009.
Riken Research [Jul. 21, 2015 searched], "Dwarf Plant Provides Insights into Cellular Development," online press in 60 seconds, Internet <URL:http://www.riken.jp/~/media/riken/pr/press/2007/2007/20071204_1/20071204_1.pdf>.
Aug. 4, 2015 Notification of Reasons for Refusal issued in Japanese Application No. 2013-049689.

* cited by examiner

Primary Examiner — Matthew R Keogh
(74) *Attorney, Agent, or Firm* — Oliff PLC

(57) ABSTRACT

A method of increasing the biomass of a plant that includes planting a plant having plant cells carrying an exogenous gene that encodes a thermophilic restriction enzyme that promotes double-stranded DNA breakage, and growing the plant at least until after true leaf development, wherein the mean biomass of plants having the plant cells carrying the exogenous gene that are grown at least until after true leaf development is increased in comparison with the mean biomass of plants of the same species that do not carry the exogenous gene that are grown for the same amount of time.

9 Claims, 9 Drawing Sheets

METHOD FOR INCREASING PLANT BIOMASS USING AN EXOGENOUS GENE ENCODING A THERMOPHILIC RESTRICTION ENZYME

CROSS REFERENCE TO RELATED APPLICATIONS

This application claims priority to Japanese Patent Application No. 2013-49689 filed on Mar. 12, 2013, the contents of which are incorporated herein by reference in their entirety.

TECHNICAL FIELD

The present Description relates to increasing production of plant biomass.

DESCRIPTION OF RELATED ART

As the world's population increases, a concern over the eventual food crisis has been growing on a global scale due to environmental pollution, global warming and other factors. Under these circumstances, there is a greater need to increase production of plant biomass. Increasing the production of plant biomass is also important as a strategy for preventing global warming by reducing emissions of greenhouse gasses from plants.

Promoting the initial growth of plants gives them an advantage in competition against weeds, and is a significant factor in obtaining large yields. Enabling plants to expand their light-receiving surfaces rapidly without being overwhelmed by weeds is a way of promoting growth by increasing photosynthesis.

For example, the elongation of the embryonic axis (as in bean sprouts for example) is closely associated with increased ploidy and cell enlargement by endoreduplication. "Endoreduplication" is a cell cycle in which DNA is replicated without cell division. Attempts have therefore been made to promote initial plant growth by inducing endoreduplication, either in a whole individual plants or in specific tissues (WO 2008/120410; Lieven De Veylder et al., The EMBO Journal Vol. 21 No. 6 pp. 1360-1368; Takashi Ishida et al, The Plant Cell, Vol. 21 2284-2297; Keiko Sugimoto et al., PNAS, 102(51):18736-41).

WO 2008/120410, De Veylder et al., and Sugimoto et al. disclose genes having endoreduplication inducing effects, while Ishida et al. specifies a gene capable of inducing endoreduplication by deletion.

However, in WO 2008/120410 for example, although root length, cotyledon size and embryonic axis length are increased by the onset of endoreduplication, growth is inhibited after true leaf development, and biomass is reduced. Moreover, De Veylder et al., Ishida et al., and Sugimoto et al. disclose that the plant become stunted and the roots are shorter when endoreduplication is induced.

BRIEF SUMMARY

As discussed above, various means have been studied for inducing endoreduplication. However, although endoreduplication promotes initial growth of plants, it also causes stunting. Thus, it has not been practical to increase plant biomass by endoreduplication. This Description provides a gene that is effective for increasing production of plant biomass, and the use of this gene.

The inventors searched for genes that would be useful for inducing endoreduplication increasing by plant cell introduction and for increasing biomass quantity. As a result of exhaustive research and analysis, the inventors arrived at the finding that endoreduplication is induced and the biomass quantity is also increased in transgenic plants transformed with the TaqI gene. According to the disclosure of the present description, the following teachings are provided based on these findings.

(1) A plant biomass production method, comprising growing a plant having plant cells carrying an exogenous gone that promotes double-stranded DNA breakage, wherein the biomass of the plant is increased.

(2) The production method according to (1), wherein the biomass of the plant after true leaf development is increased.

(3) The production method according to (1) or (2), wherein the exogenous gene promotes production of a protein having double-stranded DNA breakage activity in plant cells.

(4) The production method according to any of (1) to (3), wherein the exogenous gene is a gene coding for a protein having double-stranded DNA breakage activity.

(5) The production method according to any of (1) to (4), wherein the exogenous gene is a gene coding for an endonuclease.

(6) The production method according to any of (1) to (5), wherein the exogenous gene has 95% or greater identity with the amino acid sequence represented by SEQ ID NO:2, and codes for a protein having double-stranded DNA breakage activity.

(7) The production method according to any of (1) to (6), wherein the exogenous gene is provided so as to be operable by the cauliflower mosaic virus 35S promoter or *Arabidopsis thaliana* SIG2 promoter.

(8) The production method according to any of (1) to (7), wherein the expressed amount of a RAD51 ortholog gene in the plant cells is less than two times the expressed amount in the plant cells of a host.

(9) A plant production method, comprising:
introducing an exogenous gene that promotes double-stranded DNA breakage into plant cells and obtaining transformed plant cells; and
obtaining a plant which has acquired biomass increasing ability from the transformed plant cells.

(10) A transformed plant having plant cells carrying an exogenous gene that promotes double-stranded DNA breakage, and having increased ploidy.

(11) A plant acquired by hybridization using as a parent plant a transformed plant having plant cells carrying an exogenous gene that promotes double-stranded DNA breakage, and having increased ploidy.

(12) A seed of the plant according to (10) or (11).

(13) A method for producing a plant having biomass increasing ability, wherein a first plant that is a plant according to (10) or (11) is hybridized with a second plant to obtain a plant having biomass increasing ability.

(14) A method for producing a useful substance, comprising fermenting the biomass of the plant according to (10) or (11) as a raw material.

(15) A plant biomass increasing agent, comprising DNA coding for a protein having double-stranded DNA breakage activity.

DETAILED DESCRIPTION

Figure 1:
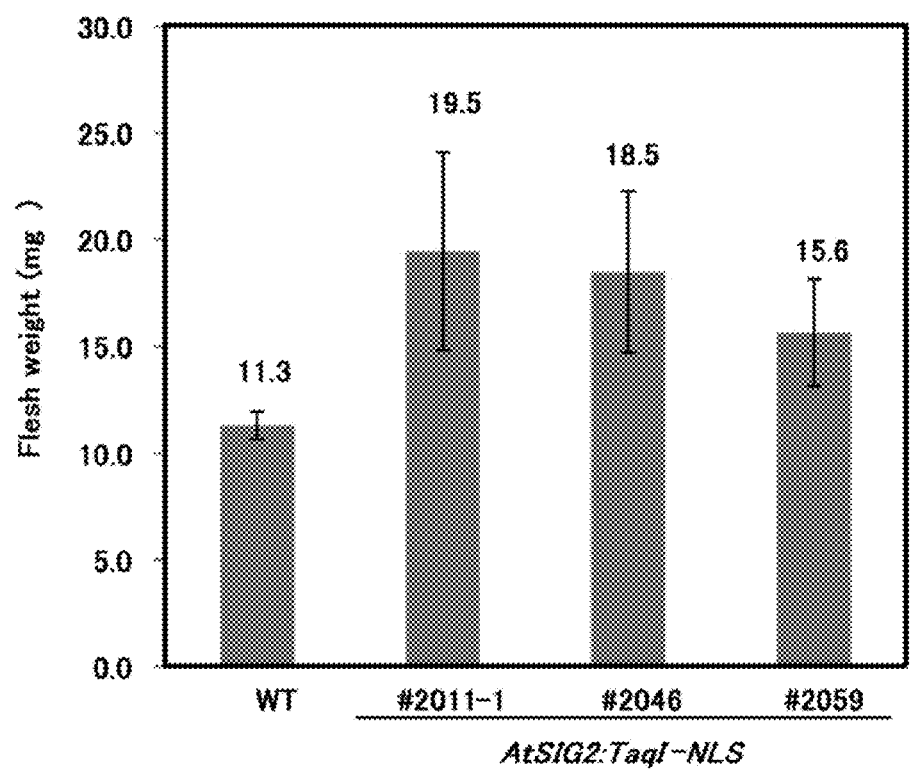
FIG. 1 shows biomass quantity in an AtSIG2:TaqI-NLS transgenic strain.

This Description relates to a gem effective for increasing production of plant biomass, and to a use therefor. This Description by the present inventors is based on the introduction into plant cells of an exogenous gene that promotes double-stranded DNA breakage, resulting in successful plant growth and increased biomass The inventors focused on a cell cycle called endoreduplication. To induce endoreduplication, the inventors focused on genes that promote double-stranded DNA breakage, and introduced one such gene, DNA coding for the TaqI protein, into plant cells. By growing plants having these cells, the inventors also succeeded in obtaining individual plants with increased biomass quantity.

With this Description, it is possible to increase biomass quantity by growing plants having plant cells carrying a gene that promotes double-stranded DNA breakage.

This production method is particularly useful in the fields of agriculture, energy production from biomass, and chemical engineering.

In this Description, "endoreduplication" is a cell cycle in which DNA is replicated without cell division. In this Description, "ploidy" means the property of carrying multiple genomes within the cell nucleus. A genome is a set of chromosomes having the minimum genes necessary for the survival of an organism. Given C as the quantity of DNA in one genome set, a diploid carrying two genome sets can be represented by 2C. Similarly, tetraploid, octoploid, 16-ploid and 32-ploids can be represented by 4C, 8C, 16C and 32C, respectively. The ploidy of plant cells tends to be increased by endoreduplication.

Ploidy can be evaluated by measurement using flow cytometry. Specifically, leaves of the plant are cut off, and subjected to nucleus extraction and DAPI staining of the genome DNA. Next, the nuclei after genome DNA staining are subjected to flow cytometry to measure the ploidy level of the leaf cells.

For example, because endoreduplication occurs independently in each cell, the ploidy of each cell is different. The degree of ploidy produced by endoreduplication is preferably evaluated in terms of the endoreduplication ratio, which is expressed by the following formula:

Endoreduplication ratio=$(8C+16C+32C)/(2C+4C+8C+16C+32C)\times100$ (wherein 2C, 4C and other ploidy numbers represent the number of cells with that ploidy).

In the disclosure of the Description below, a gene that promotes double-stranded DNA breakage, a transformed plant, a plant biomass increasing agent, a method for producing plant biomass and the like are explained in order. For ease of explanation, the gene, the protein coded by the gene, and plant body etc. will be explained before the production method.

(Gene that Promotes Double-Stranded DNA Breakage)

This Description discloses a gene that promotes double-stranded DNA breakage. This gene may be a gene that promotes production of a protein that promotes double-stranded DNA breakage, or a gene coding for such a protein. This gene may also be a gene coding for an endonuclease. An endonuclease is an enzyme that breaks down nucleic acids by hydrolyzing phosphodiester bonds. The endonuclease may be a restriction enzyme. Genes coding for endonucleases are widely present in microorganisms as well as in animals and plants, and one can be selected appropriately from genes coding for known endonucleases.

A TaqI gene having the nucleotide sequence represented by SEQ ID NO:1 is one example of the gene of the present invention. The TaqI gene is DNA coding for the TaqI protein, which is a restriction enzyme.

Because the TaqI gene is thought to occur in a wide range of microorganisms including *Thermus thermophilus* and other bacteria in the *Thermus* genus, the gene of the present invention encompasses homologous genes that occur in *Thermus* bacteria and other microorganisms. "Homologous genes" are genes coding for proteins that are functionally equivalent to the TaqI protein in various plants. Examples of such proteins include, but are not limited to, mutants, alleles, variants and homologs of the protein, partial peptides of the protein, and fused proteins with other proteins and the like. Each protein is explained in detail below.

The form of the gene of the present invention is not particularly limited as long as it can code for a protein having biomass increasing ability, and the gene of the present invention includes not only genome DNA but also cDNA, chemically synthesized DNA and the like. The gene of the present invention also includes DNA having any nucleotide sequence based on degeneracy of the genetic code as long as it codes for the protein described below.

(Suppression of RAD51 Gene Expression Promotion)

In this description, "suppression of RAD51 gene expression promotion" means that the expressed amount of the RAD51 gene and its ortholog genes is decreased less than the expressed amount in the host cells. The expressed amount of the RAD51 gene and its ortholog genes is preferably less than 3 times the expressed amount in the host cells. The RAD51 protein encoded by the RAD51 gene is known to have the function of repairing DNA damage when double-stranded DNA is broken. That is, with the gene of the present invention DNA repair become more difficult when double-stranded DNA is broken. The expressed amount is more preferably less than 2 times or even more preferably 1.5 times.

In general, double-stranded DNA breakage increases the expressed amount of RAD51, and the cell's checkpoint function operates to inhibit cell division. Cell division is important for plant growth after true leaf development, and it is thought that the plant becomes stunted when this is inhibited.

To suppress expression promotion of RAD51 and the like, it is desirable to use, as the gene of the present invention, a gene that does not induce expression of the RAD51 gene and RAD51 ortholog genes at a transcription level. In this case, the expressed amount of the RAD51 gene and its ortholog genes is preferably less than 3 times the expressed amount in host cells at the transcription level. Preferably it is less than 2 times, or more preferably less than 1.5 times, or still more preferably less than 1.2 times, or most preferably less than 1.1 times. Examples of such genes include genes that promote double-stranded DNA breakage such as the TaqI gene.

The method of promoting double-stranded DNA breakage without inducing expression of the RAD51 gene and RAD51 ortholog genes at the transcription level may be a method that does not use a gene. For example, it may involve artificial exposure to irradiation with gamma rays, x-rays or a heavy ion beam at a weak level. A compound such as breomycin or zeomycin that induces double-stranded DNA breakage may also be applied to the cells.

(Proteins that Promote Double-Stranded DNA Breakage)

As discussed above, genes that promote double-stranded DNA breakage include genes that stimulate production of proteins that promote double-stranded DNA breakage, and genes that code for such proteins. A protein that promotes double-stranded DNA breakage (hereunder called the protein of the present invention) is a nucleolytic enzyme capable of cleaving double-stranded DNA. For example, there are nucleases capable of breaking down DNA and RNA, and deoxyribonucleases capable of breaking down DNA but not RNA. Classified according to the mode of cleavage, there are endonucleases and exonucleases. Endonucleases are enzymes that cleave nucleic acids internally, and include deoxyribonucleases in mammals and micrococcal nuclease. Exonucleases are enzymes that remove nucleotides one by one from the ends of nucleic acids, and include Ba131 nuclease, exonuclease I, exonuclease III and λ-exonuclease for example. Considering the different modes of cleavage, it is thought that endonucleases are more likely than exonucleases to promote DNA repair, and therefore to increase the ploidy of plant cells and increase the biomass of the plant body. Moreover, an endonuclease may also be a restriction enzyme. The number of bases recognized by the restriction enzyme may be 4 to 8. Moreover, it may be a restriction enzyme that cleaves double-stranded DNA straight across with blunt ends, or a restriction enzyme that cleaves sticky ends each with one strand protruding. Examples of restriction enzymes include TspRI, Tsp45I, Sse9I, MseI, CviAII and the like. MspI, DpnI, HaeIII, AvaII, EcoRI, EcoRII, HinfI, XbaI, HpaI, NotI, SwaI and SgrAI are preferred, and TaqI is more preferred. The TaqI protein encoded by the TaqI gene is a restriction enzyme having the amino acid sequence represented by SEQ ID NO:2. When the TaqI protein recognizes the 4-base sequence 5'-TCGA-3', it makes a cut between T and C, cleaving the double-stranded DNA with sticky ends. The TaqI may be in the form of a protein having the amino acid sequence represented by SEQ ID NO:2, and also may be a mutant thereof.

Any restriction enzyme gene can be used as the restriction enzyme gene as long as it codes for a restriction enzyme capable of introducing double-stranded breaks into a specific sequence site in the genome DNA of plant cells. For example, a restriction enzyme is preferably an enzyme having a 4 to 6-base recognition sequence, or more preferably one having a 4 to 5-base recognition site, or most preferably one having a 4-base recognition site.

A restriction enzyme that is activated under conditions different from the culture conditions of the plant cells is preferably used as the restriction enzyme. "Conditions different from ordinary culture conditions" may be any conditions that can be selected by a person skilled in the art, but for example may be conditions involving addition of a substance (such as metal ions or the like) necessary for activation of the restriction enzyme used, or temperature conditions necessary for activation of the restriction enzyme. In particular, it is desirable to use a restriction enzyme that is derived from a thermophile and has an optimum temperature at a higher temperature range than the culture temperature of the plant cells. For example, the optimum temperature for TaqI and Tsp45I is 65° C., and the optimum temperature for Sse9I is 55° C.

Thus, using a restriction enzyme that is activated under conditions different from the culture conditions of the plant cells, it is possible to first cause expression of the restriction enzyme gene in the plant cells, and then choose whether to activate the restriction enzyme under those conditions, or to keep activation at a low level by not applying those conditions. For example, if the plant cells are killed because activation of the restriction enzyme is too great when the restriction enzyme gene is expressed in plant cells, it is possible to avoid killing the plant cells by not applying the conditions and maintaining activation of the restriction enzyme at a low level.

The protein of the present invention may be any protein that has double-stranded DNA cleavage activity and can increase plant biomass by endoreduplication. Typical examples are proteins that produce the desired endoreduplication ratio as discussed below. One mode of this protein is a protein having an amino acid sequence comprising the amino acid sequence represented by SEQ ID NO:2 with one or more amino acids substituted, deleted, inserted and/or added therein, which is a protein that is functionally equivalent to the TaqI protein. Using the protein represented by SEQ ID NO:2 as the standard, other proteins can be regarded as mutants of this standard protein.

The number of amino acids that are mutated is not particularly limited, but is normally 20 or fewer amino acids, or preferably 10 or fewer amino acids, or more preferably 6 or fewer amino acids, or still more preferably 3 or fewer amino acids, or yet more preferably 2 or fewer amino acids. The mutated amino acid residues are preferably mutated into amino acids in which the properties of the amino acid side chains are retained (this is known as conservative amino acid substitution). For example, amino acids can be classified generally into two types, hydrophobic amino acids (A, I, L, M, F, P, W, Y, V) and hydrophilic amino acids (R, D, N, C, E, Q, G, H, K, S, T) according to properties of their side chains. Moreover, amino acids can also be classified based on the structures of their side chains, into amino acids having aliphatic side chains (G, A, V, L, I, P), amino acids having side chains containing hydroxyl groups (S, T, Y), amino acids having side chains containing sulfur atoms (C, M), amino acids having side chains containing carboxylic acid and amide groups (D, N, E, Q), amino acids having side chains containing bases (R, K, H), amino acids having side chains containing aromatic groups (H, F, Y, W) and the like. Also, for example classification of amino acids according to the mutational matrix is also well known (Taylor 1986, J. Theor. Biol. 119, 205-218; Sambrook J. et al., Molecular Cloning 3rd ed. A7.6-A7.9, Cold Spring Harbor Lab. Press, 2001). To summarize these classification, there are aliphatic amino acids (L, I, V), aromatic amino acids (H, W, Y, F), charged amino acids (D, E, R, K, H), positively charged amino acids (R, K, H), negatively charged amino acids (D, E), hydrophobic amino acids (H, W, Y, F, M, L, I, V, C, A, G, T, K), polar amino acids (T, S, N, D, E, Q, R, K, I, W, Y), small amino acids (P, V, C, A, G, T, S, N, D), very small amino acids (A, G, S) and large (non-small) amino acids (Q, E, R, K, H, W, Y, F, M, L, I) (all letters in brackets are single-letter amino acid designations).

It is well known that a polypeptide comprising an amino acid sequence that has been modified by one or more deletions or additions of amino acid residues and/or amino acid substitutions retains the biological activity of the amino acid sequence.

Another mode of the protein of the present invention is for example a protein coded for by DNA that hybridizes under stringent conditions with DNA consisting of the nucleotide sequence represented by SEQ ID NO:1, which is functionally equivalent to the TaqI protein. With such DNA, the identity between the nucleotide sequence as a whole and the nucleotide sequence represented by SEQ ID NO:1 is typically at least 30%, or preferably at least 40%, or more preferably at least 50%, or still more preferably at least 70%, or yet more preferably at least 80%, or even more preferably at least 85%, or even more preferably at least 90%, or even more preferably at least 95%, or most preferably at least 98%, or ideally at least 99%.

Another mode of the protein of the present invention is for example a protein that has an amino acid sequence having at least 60% identity with the amino acid sequence represented by SEQ ID NO:2, and that is functionally equivalent to the TaqI protein. The degree of identity is at least 30%, or preferably at least 40%, or more preferably at least 50%, or still more preferably at least 60%, or yet more preferably at least 70%, or even more preferably at least 80%, or even more preferably at least 85%, or even more preferably at least 90%, or even more preferably at least 95%, or most preferably at least 98%, or ideally at least 99%.

In this Description, "functionally equivalent" means that the protein in question has a biological function or biochemical function equivalent to that of a protein (TaqI) or the like having the amino acid sequence represented by SEQ ID NO:2. A biological function or biochemical function of TaqI is for example the function of promoting double-stranded DNA breakage. When a transformed plant is obtained having DNA encoding this protein introduced therein using conspecific materials and conspecific methods, the endoreduplication ratio (discussed above) as measured under the same conditions is preferably at least 12.5%. More preferably it is at least 13.0%, or still more preferably at least 15.0%, or yet more preferably at least 20.0%, or even more preferably at least 25.0%, or most preferably at least 40.0%.

Methods of isolating homologous genes and the like that are well known to those skilled in the art include hybridization techniques (Southern, E. M., Journal of Molecular Biology. Vol. 98, 503, 1975) and polymerase chain reaction (PCR) techniques (Saiki, R. K. et al., Science vol. 230, 1350-1354, 1985; Saiki, R. K. et al., Science vol. 239, 487-491, 1988) are well known to those skilled in the art. That is, it is an ordinary matter for a person skilled in the art to isolate homologous genes to the TaqI gene from various plants using the nucleotide sequence represented by SEQ ID NO:1 or a part thereof as a probe with oligonucleotides that specifically hybridize with the TaqI gene as primers.

A hybridization reaction is normally performed under stringent conditions to isolate DNA coding for a homologous gene. Stringent hybridization conditions can be selected appropriately by a person skilled in the art. As one example, pre-hybridization is first performed overnight at 42° C. in a hybridization solution containing 25% formamide (or 50% formamide under more stringent conditions), 4×SSC, 50 mM Hepes pH 7.0, 10×denhardt's solution and 20 μg/ml denatured salmon sperm DNA, after which a labeled probe is added and hybridization is performed by maintaining the temperature at 42° C. overnight. The washing solution and temperature conditions for the subsequent washing can be about (1×SSC, 0.1% SDS, 37° C.) or (0.5×SSC, 0.1% SDS, 42° C.) for more stringent conditions, or (0.2×SSC, 0.1% SDS, 65° C.) for still more stringent conditions. By making the washing conditions for hybridization more stringent, it is possible to isolate DNA having a higher degree of homology with the probe sequence. However, these combinations of SSC, SDS and temperature conditions are only examples, and a person skilled in the art can achieve a similar level of stringency by appropriately combining these and other factors that determine hybridization stringency (such as probe concentration, probe length, hybridization reaction time, etc.).

Identity of the isolated DNA is at least 50%, preferably at least 70%, more preferably at least 90% (for example, at least 95%, 96%, 97%, 98% or 99%) in sitity of the amino acid sequence. Identity can be determined by programs such as BLASTN (nucleuic acid level) or BLASTX (amino acid level) (Altschul et al. J. Mol. Biol., 215: 403-410, 1990). These programs are constructed based on the algolithm by Karlin and Altschul (Proc. Natl. Acad. Sci. USA, 87:2264-2268, 1990, Proc. Natl. Acad. Sci. USA, 90: 5873-5877, 1993). When a base sequence is analyzed by BLASTN, for example, score=100, wordlength=12 are used as parameters. When an amino acid sequence is analyzed by BLASTX, for example, score=50, wordlength=3 are used as parameters. When an amino acid sequence is analyzed by Gapped BLAST, the proctols in Altschul et al. (Nucleic Acids Res. 25: 3389-3402, 1997) can be used. When BLAST and Gapped BLAST are used, default parameters in each program can be used. The specific analysis methods are known to the person skilled in the art.

(Plant Body)

There are no particular limits on the target plant, or in other words on the type of plant used to produce a mutant plant, but examples include dicots and monocots, including plants in the Brassicaceae, Graminiae, Solanaceae, Leguminosme, Salicaceae and other families (listed below).

Brassicaceae: *Arabidopsis thaliana*, *Brasica rapa*, *Brassica napus*, cabbage (*Brassica oleracea* var. *capitata*), Napa cabbage (*Brassica rapa* var. *pekinensis*), *Brassica rapa* var. *chinensis*, turnip (*Brassica rapa* var. *rapa*), *Brassica rapa* var. *hakabura*, *Brassica rapa* var. *lancinifolia*, *Brassica rapa* var. *peruviridis*, Chinese cabbage (*Brassica rapa* var. *chinensis*), daikon (*Brasica Raphanus sativus*), wasabi (*Wasabia japonica*), etc.

Solanaceae: Tobacco (*Nicotiana tabacum*), eggplant (*Solanum melongena*), potato (*Solaneum tuberosum*), tomato (*Lycopersicon lycopersicum*), pepper (*Capsicum annuum*), petunia, etc.

Leguminosae: Soy beans (*Glycine max*), peas (*Pisum sativum*), fava beans (*Vicia faba*), wisteria (*Wisteria floribunda*), peanuts (*Arachis hypogaea*), bird's foot trefoil (*Lotus corniculatus* var. *japonicus*), garden beans (*Phaseolus vulgaris*), azuki beans (*Vigna angularis*), Acacia, etc.

Asterceae: Chrysanthemum (*Chrysanthemum morifolium*), sunflower (*Helianthus annuus*) etc.

Arecaceae: Oil palm (*Elaeis guineensis, Elaeis oleifera*), coconut palm (*Cocos nucifera*), date palm (*Phoenix dactylifera*), carnauba palm (*Copernicia*), etc.

Anacardiaceae: Japanese wax tree (*Rhus succedanea*), cashew (*Anacardium occidentale*), lacquer tree (*Toxicodendron vernicifluum*), mango (*Mangifera indica*), pistachio (*Pistacia vera*), etc.

Cucurbitaceae: Squash (*Cucurbita maxima, Cucurbita moschata, Cucurbita pepo*), cucumber (*Cucumis sativus*), snake gourd (*Trichosanthes cucumeroides*), bottle gourd (*Lagenaria siceraria* var. *gourda*), etc.

Rosaceae: Almond (*Amygdalus communis*), rose (*Rosa*), strawberry (*Fragaria*), cherry (*Prunus*), apple (*Malus pumila* var. *domestica*), etc.

Caryophyllaceae: Carnation (*Dianthus caryophyllus*), etc.

Salicaceae: Poplar (*Populus trichocarpa, Populus nigra, Populus tremula*), etc.

Gramineae: Corn (*Zea mays*), rice (*Oryza sativa*), barley (*Hordeum vulgare*), wheat (*Triticum aestivum*), bamboo (*Phyllostachys*), sugar cane (*Saccharum officinarum*), napier grass (*Pennsetum pupureum*), *Erianthus ravenae, Miscanthus virgatum*, sorghum, switch grass (*Panicum*), etc.

Liliaceae: Tulip (*Tulipa*), lily (*Lilium*), etc.

Myrtaceae: Eucalyptus (*Eucalyptus camaldulensis, Eucalyptus grandis*), etc.

(Plant Cells)

Plant cells from a monocot or dicot plant can be used as the plant cells. The cells may also be from a cereal plant. Examples of plant cells include cells of the various plant species described above. In addition to suspension cultured cells and other cultured cells, plant cells include protoplasts and callus cells. Plant cells also include cells in the plant body, including shoot primordia, multiple buds and hairy roots, as well as leaf sections and the like.

(Plant Body and Plant Biomass Quantity)

The plant body includes the plant leaves, stems, flowers, seeds and roots. In this Description, increasing the biomass quantity means increasing the weight of the plant body. Weight may mean either dry weight or wet weight. The weight may be the weight of the whole plant body or the weight of a part of the plant body, such as the leaves alone, the leaves and stems, the seeds alone or the roots alone. For example, when the aim is to obtain biomass ethanol from corn, the biomass quantity of the corn is preferably that of the seeds, but may also be that of the leaves and stems. Having plant biomass increasing ability preferably means that the biomass quantity is increased by at least 2%, or preferably at least 5%, or more preferably at least 10%, or still more preferably at least 20%, or yet more preferably at least 30%, or even more preferably at least 35%, or even more preferably at least 40%, or even more preferably at least 45%, or most preferably at least 50% in comparison with a plant body in which the gene of the present invention is not expressed.

(Plant Body after True Leaf Development)

A leaf that is already present in the embryo inside the plant seed is called a cotyledon. When the seed germinates, the cotyledon emerges first. Then the true leaves emerge in the process of plant growth. That is, the true leaves are the normal leaves other than the cotyledon. The number of days from sowing to true leaf development differs according to the plant, and for example the true leaves of *Arabidopsis thaliana* develop in about 7 days. As discussed above, with existing techniques plant growth after true leaf development is inhibited by induced endoreduplication, and biomass is reduced (WO 2008/120410). By contrast, with the technique disclosed in this Description the biomass can be increased after true leaf development.

(Vector)

The vector of this Description may include the aforementioned DNA. In addition to containing the aforementioned DNA, the vector of the invention may also be designed to amplify expression of the DNA of the present invention in plant cells. The vector of the invention may be designed to amplify expression of the gene of the present invention by introducing the gene of the present invention as exogenous DNA, regardless of whether or not the gene of the present invention is present as an endogenous gene on the chromosome in the host cells (plant cells). In particular, a vector containing DNA having the nucleotide sequence represented by SEQ ID NO:1 is preferably linked downstream from a promoter capable of amplifying the expression or specifically increasing the expressed amount of this DNA, in such a way that it can be controlled by the promoter. However, this does not exclude vectors that are designed to amplify expression of the endogenous gene of the present invention on the chromosome in plant cells by homologous recombination or the like.

When the vector of the invention is designed to introduce and cause expression of the gene of the present invention in plant cells as exogenous DNA, it can be provided with a promoter that is transcribable in plant cells, together with the gene of the present invention, which is linked so as to be operable under the control of the promoter. It may also comprise a terminator containing polyA. Examples of such promoters include promoters for constantly or inductively causing expression of the gene of the present invention for example. Examples of promoters for causing constant expression include the cauliflower mosaic virus 35S promoter (Odell et al., 1985 Nature 313:810), rice actin promoter (Zhang et al. 1991 Plant Cell 3:1155), corn ubiquitin promoter (Comejo et al. 1993 Plant Mol. Biol. 23:567) and the like. Promoters for inductively causing expression of the gene include promoters that are known to cause expression in response to external factors such as infection or incursion by fungi, bacteria or viruses, low temperatures, high temperatures, drying, UV irradiation, and application of specific compounds. Examples of such promoters include a rice chitinase gene promoter (Xu et al. 1996 Plant Mol. Biol. 30:387), tobacco PR protein gene promoter (Ohshima et al. 1990 Plant Cell 2:95), rice "lip19" gene promoter (Aguan et al. 1993 Mol. GenGenet. 240:1), rice "hsp80" gene and "hsp72" gene promoters (Van Breusegem et al. 1994 Planta 193:57), *Arabidopsis thaliana* "rab16" gene promoter (Nunday et al. 1990 Proc. Natl. Acad. Sci. USA 87:1406), parsley chalcone synthase gene promoter (Schulze-Lefert et al. 1989 EMBO J. 8:651), corn alcohol dehydrogenase gene promoter (Walker et al. 1987 Proc. Natl. Acad. Sci. USA 84:6624) and the like. Another example is the *Arabidopsis thaliana* SIG2 promoter.

The vector of the invention may also be one that causes the protein of the present invention to be produced as a recombinant protein in *E. coli*, yeasts, animal and plant cells, insect cells and other host cells. In this case, the vector of the invention can be provided with the gene of the present invention under the control of a promoter that is operable in suitable host cells.

The vector of the invention can be constructed by a person skilled in the art using various plasmids and other commercially available materials known to those skilled in the art. In addition to the plasmids "pBI121", "pBI221", "pBI101" and the like (all from Clontech) for example, it can be constructed using a vector that causes the gene of the present invention to be expressed in plant cells for purposes of preparing a transformed plant body. Introduction of this vector of the invention into host cells is explained below.

(Transformed Plant Cells and Transformed Plant Body)

The disclosure of this Description provides transformed cells having the vector of the invention introduced therein and carrying the gene of the present invention. The transformed plant body disclosed in this Description comprises such transformed cells. Expression of the gene of the present invention is greater in this transformant than before transformation. The gene of the present invention to be amplified may be a gene that is endogenous in the plant body, or an exogenous gene. It may also be both. Amplification of gene expression means either that the expressed amount of the gene (the amount of the primary transcription product of the gene of the present invention, the produced amount of the protein coded for by the gene of the present invention) is greater than before transformation, or that the activity of the protein is greater than before transformation. It may also be that the expressed amount of the gene of the present invention and the activity of the protein of the present invention itself are both amplified as a result of amplification of the expression of a gene of the present invention.

The mode of amplification of gene expression is not particularly limited. For example, a promoter operable in plant cells and the gene of the present invention linked so as to be operable by the promoter may be carried as exogenous DNA on or outside the chromosomes of the plant cells. The gene of the present invention linked to the promoter may be endogenous or exogenous to the plant cells. To increase the activity of a promoter for the endogenous gene of the present invention, all or part of the promoter region on the chromosome may be substituted or the like, or the promoter region may be substituted together with the endogenous gene.

The transformed plant body of the invention can be obtained by regenerating a plant body from the transformed cells of the invention. The vector can be introduced into the plant cells using various methods known to those skilled in the art, such as polyethylene glycol methods, electroporation. *Agrobacterium*-mediated methods, particle gun methods or the like. Examples include various methods such as gene introduction into the protoplast with polyethylene glycol (Datta, S. K. (1995) in Gene Transfer to Plants (Potrykus I and Spangenberg Eds.) pp 66-74), gene introduction into the protoplast by electrical pulse (Toki et al. (1992) Plant Physiol. 100, 1503-1507), direct introduction of the gene into cells with a particle gun (Christou et al. (1991) Bio/technology, 9:957-962), and gene introduction via an *Agrobacterium* (Hiei et al. (1994) Plant J. 6:271-282). Regeneration of a plant body from the transformed cells can be accomplished by methods known to those skilled in the art according to the type of plant cells (Toki et al. (1995) Plant Physiol. 100:1503-1507). For example, the method of Akama et al (Plant Cell Reports 12:7-11 (1992)) can be used for *Arabidopsis thaliana*, the method of Fujimura et al (Plant Tissue Culture Lett. 2:74 (1995)) for rice, and the method of Shillito et at (Bio/Technology 7:581 (1989)) or the method of Gorden-Kamm et al (Plant Cell 2:603(1990)) for corn.

Regeneration of a plant body from the transformed plant cells can be accomplished by methods known to those skilled in the art according to the type of plant cells (Toki et al. (1995) Plant Physiol. 100:1503-1507). In the case of rice for example, a number of techniques have already been established for creating transformed plants, such as a method of introducing a gene into the protoplast with polyethylene glycol and then regenerating a plant (suited to indica-type rice varieties) (Datta, S. K (1995) in Gene Transfer to Plants (Potrykus I and Spangenberg Eds.) pp 66-74), a method of introducing a gene into the protoplast by electric pulse and then regenerating a plant (suited to Japanese rice) (Toki et al. (1992) Plant Physiol. 100, 1503-1507), a method of directly introducing a gene into cells with a particle gun and then regenerating a plant (Christou et al. (1991) Bio/technology, 9:957-962) and a method of introducing a gene via an *Agrobacterium* and then regenerating a plant (Hiei et al. (1994) Plant J. 6:271-282), and these are widely used in the technical field of the invention of the application. These methods can be used favorably in the present invention.

Double-stranded DNA breakage may be accompanied by endoreduplication in the transformed cells of the transformed plant. In endoreduplication, the DNA is replicated, but no cell division occurs. This increases the ploidy of the plant cells.

A transformed plant of the invention obtained in this way may have plant cells with increased ploidy that carry the exogenous gene of the present invention. Increased ploidy her means that the endoreduplication ratio of the plant or a part thereof (determined for example according to the site of the target biomass (leaves, etc.)) is preferably 12.5% or more. Such a plant has greater ploidy than the wild strain, and is expected to have larger plant cells. The ratio is more preferably 13.0% or more, or still more preferably 15.0% or more, or yet more preferably 20.0% or more, or even more preferably 25.0% or more, or most preferably 40.0% or more.

If a transformed plant is obtained that has the gene of the present invention built into its genome, it is then possible to obtain plants by hybridizing this plant. It is also possible to obtain reproductive materials (such as seeds, fruits, cut ears, tubers, tuberous roots, stalks, callus, protoplast or the like) from the plant or a plant or clone obtained by hybridizing the plant, and mass produce the plant from this material. The disclosure of this Description includes the aforementioned (1) plant cells with increased ploidy carrying the gene of the present invention and (2) plant having these cells, as well as (3) plants and clones obtained by hybridizing this plant, and (4) reproductive material of the plant and its descendants and clones. This Description also discloses a seed of a plant of (1) or (3).

The transformed plant created in this way has acquired or improved biomass increasing ability, and has increased biomass quantity.

(Plant Biomass Production Method)

The plant biomass production method disclosed in this Description can be provided with a step of growing a plant having plant cells carrying an exogenous gene that promotes double-stranded DNA breakage. With the production method of this Description, it is possible to increase biomass quantity, and obtain a plant with a large biomass quantity. In particular, it is possible to obtain a plant having increased biomass after true leaf development, and to obtain increased plant biomass. The growing process can be determined appropriately by a person skilled in the art according to the type of the plant of the invention. The plant that is grown by the production method of the invention may be the transformed plant of the invention or a plant obtained by hybridization from this plant.

In the production method of the invention, when the protein of the present invention has a high activation temperature as in the case of TaqI, plant biomass can be obtained by growing the plant at a temperature lower than the activation temperature of the protein. In this way, the protein of the present invention can be applied in moderation to induce endoreduplication and increase biomass.

In the production method of the invention, the expressed amount of a RAD51 ortholog gene in the plant cells of the plant is preferably less than two times the expressed amount in the original plant cells (host cells). With such plant cells, the RAD51 protein serves the function of repairing DNA damage after double-stranded DNA breakage. Thus, the endoreduplication inducing effects of the introduction of a gene of the present invention and amplification are suppressed if the expressed amount of the protein is too great. The expressed amount of the RAD51 ortholog gene can be detected appropriately by a person skilled in the art by means of the protein or mRNA or the like.

(Plant Production Method)

The plant production method disclosed in this Description may comprise a step of introducing an exogenous gene that promotes double-stranded DNA breakage into plant cells to obtain transformed plant cells, and a step of obtaining a plant with biomass increasing ability from the transformed plant cells. The transformed cells and the plant are obtained as explained above. Plants having acquired biomass increasing ability can be selected appropriately based on an evaluation of the size of the regenerated plants, the expressed amount of the gene of the present invention, the expressed amount of the RAD51 gene, and the ploidy (endoreduplication ratio).

In this production method of the invention, when the protein of the present invention has a high activation temperature (as in the case of TaqI for example), a plant can be obtained by cultivating transformed cells or growing a plant at a temperature lower than the activation temperature of the protein. As a result, the protein of the present invention can thus be applied in moderation to induce endoreduplication and increase biomass. Thus, a plant with biomass increasing ability can be obtained effectively with this production method of the invention even at a low cultivation temperature.

In this production method of the invention, a plant having biomass increasing ability can also be obtained by hybridization using the transformed plant as a first plant and another plant as a second plant. Moreover, in this production method of the invention a plant having biomass increasing ability can also be obtained by hybridization using a plant obtained by hybridization from a transformant as a first plant and another plant as a second plant. Such a method provides a plant obtained by hybridization, a parent of which is transformed plant with increased ploidy carrying an exogenous gene that promotes double-stranded genome DNA breakage. Hybridization techniques for obtaining desirable traits can be obtained and implemented appropriately by a person skilled in the art. Hybridization can be carried out by artificial pollination. Examples of methods of artificial pollination are a method of cutting off a flower of one plant and sprinkling the pollen onto a flower of another plant, and a method of collecting the pollen of one plant and blowing it onto a flower of another plant.

A plant obtained from a transformed plant of the invention or its hybrid is a plant obtained by hybridization using as a parent plant a transformed plant with increased ploidy carrying the exogenous gene of the present invention.

(Method of Producing Useful Substance)

The method of producing a useful substance disclosed in this Description may comprise a step of fermenting biomass of the plant of the invention as a raw material. Examples of useful substances include ethanol, butanol and other biofuels, and industrial raw materials, foodstuffs and the like. The microorganisms and fermentation conditions used in fermentation can be set appropriately by a person skilled in the art. The microorganism may be a prokaryotic microorganism such as *E. coli* or a eukaryotic microorganism such as a mold or yeast, and is preferably a yeast such as *Saccharomyces cerevisiae*.

(Method of Adjusting Biomass Quantity)

The disclosure of this Description provides a method of adjusting in plants the amount of increase in biomass quantity, wherein expression of the gene of the present invention is regulated. In the adjustment method disclosed in this Description, the degree of increase in biomass quantity can be adjusted by regulating the introduced amount of the gene of the present invention. As explained above, adjusting the introduced amount of the gene of the present invention in a plant includes preparing a plant having this characteristic by either genetic engineering or hybridization. Hybridization with another plant that lacks the gene of the present invention or in which the gene of the present invention does not function is another option.

(Method of Evaluating Plant Biomass Increasing Ability)

The disclosure of this Description provides a method for evaluating plant biomass increasing ability. That is, they provide a method having a step of performing expression analysis for the gene of the present invention in a test plant or part thereof. "Evaluating plant biomass increasing ability" includes not only evaluating the biomass increasing ability of existing varieties, but also evaluating the plant biomass increase abilities of new varieties obtained by hybridization or gene recombination. A part of a plant may be a plant organ, tissue or cells.

This evaluation method of the invention is particularly advantageous when improving varieties by plant hybridization. Compared to evaluating the existence or degree of plant biomass increasing ability in an edible part based on its phenotype, evaluation at the genetic level can contribute greatly to plant variety improvement because it is easy and accurate.

Expression analysis of the gene of the present invention can be performed by a person skilled in the art using known methods. For example, it is possible to prepare an RNA sample containing RNA from a test plant or reproductive material thereof, assay the mRNA in the sample by quantitative real time PCR, and evaluate the expressed amount based on the resulting amount of mRNA. The test plant can then be judged to have plant biomass increasing ability or enhanced ability based on the expression or expressed amount of the gene of the present invention.

A known expression analysis technique such as real time PCR or a DNA microarray using the aforementioned probes and primer can be used appropriately for expression analysis.

(Plant Biomass Increasing Agent)

The disclosure of this Description provides a plant biomass increasing agent comprising DNA coding for a protein having double-stranded DNA breakage activity. The protein of the present invention is as explained above. The TaqI protein is one example of a protein having double-stranded DNA breakage activity.

EXAMPLES

The present invention is explained in detail below with examples, but these do not limit the present invention.

Example 1

(Obtaining TaqI Gene)

The TaqI gene was amplified by PCR using the budding yeast plasmid pHS141 (Japanese Patent No. 4158920) as the template. PCR was performed with PrimeSTAR HS DNA Polymerase (Takara Bio), using primers (BamHI-TaqI-F (SEQ ID NO:3) and TaqI-ScaI-R (SEQ ID NO:4)) having added restriction enzyme sites (BamHI, SacI). The amplified TaqI gene was subcloned to a TA-Cloning pCR2.1 vector using a TOPO TA Cloning Kit (Invitrogen).

(Preparation of TaqI-NLS Gene)

A TaqI-NLS gene was prepared by PCR using the resulting TaqI gene. PCR was performed with PrimeSTAR HS DNA Polymerase using a primer (Taq-NLS-SacI-R (SEQ ID NO:5) having an added NLS sequence. The amplified TaqI-NLS gene was subcloned to a TA-Cloning pCR2.1 vector using a TOPO TA Cloning Kit (Invitrogen).

(Obtaining AtSIG2 Promoter)

Young *Arabidopsis thaliana* leaves were frozen with liquid nitrogen and ground, and used with a DNeasy Plant Mini Kit (Qiagen) to prepare genome DNA. With the prepared genome DNA as the template, the promoter part (AtSIG2 promoter) of *Arabidopsis thaliana* SIG2 (Sigma subunit of chloroplast RNA polymerase) (Atlg08540) was amplified by PCR. Primers (SalI-AtSIG2-F (SEQ ID NO:6) and AtSIG2-BamHI-R (SEQ ID NO:7)) having added restriction enzyme sites (SalI, BamhI) were used in the PCR reaction.

(Preparation of Vector pBI101N2 for Promoter Cloning)

The plant expression vector pBI121 (Clontech) was treated with the restriction enzymes HindIII and BamHI. Next, equal amounts of the oligonucleotides Linker-F2 (SEQ ID NO:8) and Linker-R2 (SEQ ID NO:9) were mixed, and left standing for 10 minutes at 96° C. and then for 2 hours at room temperature. A ligation reaction was performed with the oligonucleotide mix after standing, the restriction enzyme-treated pBI121 and a "Mighty Mix" DNA Ligation Kit (Takara Bio) to prepare the promoter cloning vector pBI101N2.

(Preparation of Promoter Cloning Vector pBI TaqI-NLS)

The prepared TaqI-NLS gene was subcloned to the prepared promoter cloning vector pBI101N2 to prepare the promoter cloning vector pBI TaqI-NLS.

(Preparation of Plant Expression Vector pBI 35S:TaqI-NLS)

The prepared Taq-NLS gene was subcloned to the plant expression vector pBI121 (containing a cauliflower mosaic virus (CaMV) 35s promoter as a promoter) to prepare the plant expression vector pBI 35S:TaqI-NLS.

(Preparation of Plant Expression Vector pBI AtSIG2:TaqI-NLS)

The obtained AtSIG2 promoter was subcloned to the prepared promoter cloning vector pBI TaqI-NLS to prepare the plant expression vector pBI AtSIG2:TaqI-NLS.

Example 2

(Introduction of TaqI Gene into *Arabidopsis thaliana* Col-0 Wild Strain)

The prepared plant expression vector pBI AtSIG2:TaqI-NLS was introduced into *Arabidopsis thaliana* Col-0 by the *Agrobacterium* method. The prepared plant expression vector pBI 35S:TaqI-NLS was also introduced into *Arabidopsis thaliana* 1406 by the *Agrobacterium* method.

Each *Arabidopsis thaliana* was transformed by the implanter method. Specifically, *Agrobacterium*-infected seeds were planted in MS agar medium (Murashige-Skoog inorganic salts, 1% sucrose, 0.05%6 MES, 0.8% Agar) containing 50 mg/l kanamycin phosphate, and grown for 2 weeks in a climate-controlled room at 22° C. with a light period of 16 hours, a dark period of 8 hours, and a light intensity of about 30 to 50 µmol/m²/sec to implement kanamycin resistance selection whereby respective *Arabidopsis thaliana* transformants were obtained.

Example 3

(Biomass Quantity of AtSIG2:TaqI-NLS Transgenic Strain and 35S:TaqI-NLS Transgenic Strain)

The resulting *Arabidopsis thaliana* transformant with the introduced AtSIG2:TaqI-NLS gene was hybridized to obtain strains #2011, #2046 and #2059 having the AtSIG2:TaqI-NLS gene inserted homozygously. Seeds of the #2011, #2046 and #2059 strains and the Col-09 wild strain were planted in MS agar medium, and grown for 3 weeks in a climate-controlled room at 22° C. with a light period of 16 hours, a dark period of 8 hours, and a light intensity of about 30 to 50 µmol/m²/sec. At this stage, each plant had already developed true leaves. FIG. 1 shows the results of measurement of the biomass of 10 to 14 individual plants of each resulting strain. As shown in FIG. 1, the mean live weights of the #2011, #2046 and #2059 strains were 19.5 mg, 18.5 mg and 15.6 mg, respectively. On the other hand, the mean biomass quantity of the Col-0 wild strain was 11.3 mg. That is, the mean biomass quantities of the #2011, #2046 and #2059 strains were 73%, 64% and 39% greater than the mean biomass quantity of the Col-0 strain, respectively. The ratio of plants with increased biomass quantity was 6/10 in the case of the #2011 strain, 6/10 in the case of the #2046 strain and 5/10 in the case of the #2059 strain.

Figure 2:
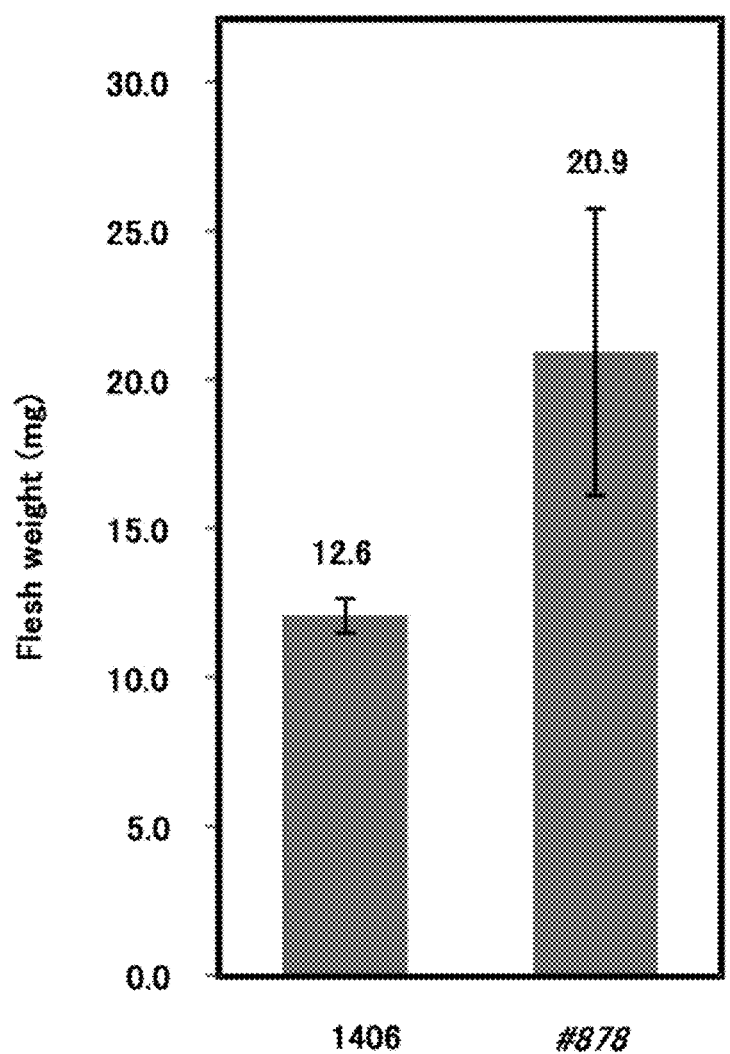
FIG. 2 shows biomass quantity in a 35S:TaqI-NLS transgenic strain.

As in the case of the AtSIG2:TaqI-NLS transgenic strain above, an *Arabidopsis thaliana* transformant with the introduced 35S:TaqI-NLS gene was hybridized to obtain a #878 strain with the introduced 35S:TaqI-NLS gene inserted homozygously. Seeds of the #878 strain and the 1406 wild strain were grown for 3 weeks under the same conditions as the AtSIG2:TaqI-NLS transgenic strain. At this stage, each plant had already developed true leaves. FIG. 2 shows, with respect to 878 strain, the results of measurement of the biomass of 10 to 14 individual plants of each resulting strain. As shown in FIG. 2, the average live weight of the #878 strain was 20.9 mg. On the other hand, the mean biomass quantity of the 1406 wild strain was 12.6 mg. That is, the mean biomass quantity of the #878 strain was 73% greater than the mean biomass quantity of the 1406 wild strain. The ratio of plants with increased biomass quantity was 4/8 in the case of the #878 strain.

Thus, it has been shown that a plant having plant cells carrying the TaqI gene has increased plant biomass.

Example 4

(Promotion of Root Elongation in 35S:TaqI-NLS Transgenic Strain)

Figure 3:
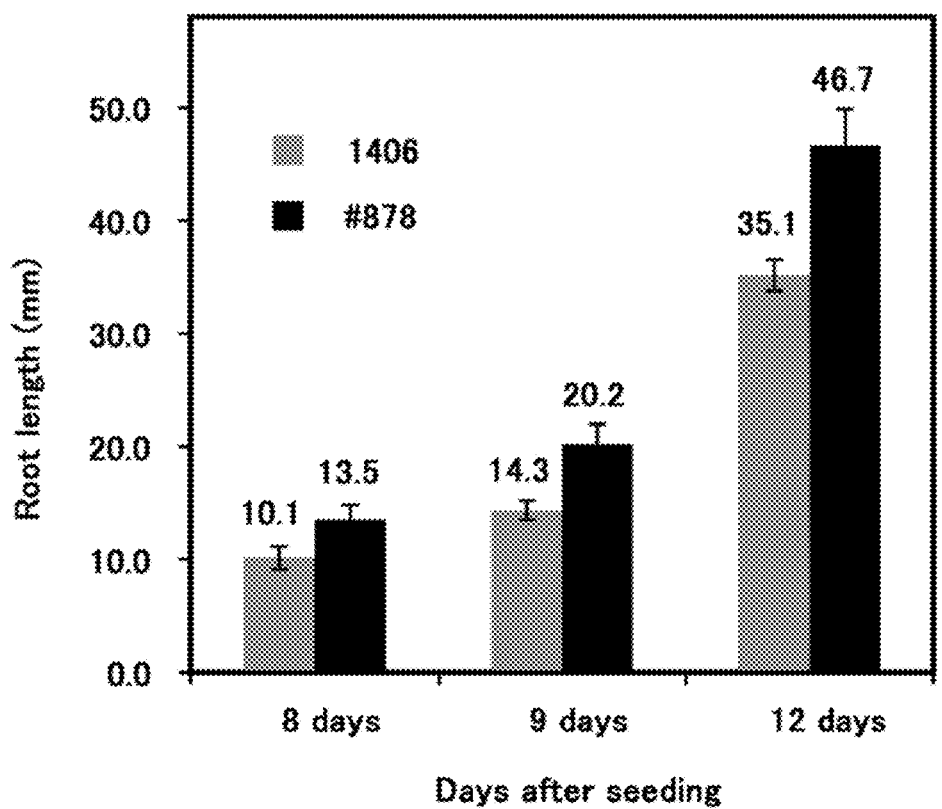
FIG. 3 shows root length in a 35S:TaqI-NLS transgenic strain.

Seeds of the aforementioned #878 strain and 1406 wild strain were planted in MS agar medium, and grown for 3 weeks in a climate-controlled room at 22° C. with a light period of 16 hours, a dark period of 8 hours, and a light intensity of about 30 to 50 µmol/m²/sec. The MS agar medium was arranged vertically so that the plant roots crawled along the surface of the agar. Root lengths were measured 8, 9 and 12 days after planting, and the mean was determined for 8 individual plants. The results are shown in FIG. 3. As shown in FIG. 3, the mean root lengths of the #878 strain after 8, 9 and 12 days were 13.5 mm, 20.2 mm and 46.7 mm, respectively. Meanwhile the mean root lengths for the 1406 strain after 8, 9 and 12 days were 10.1 mm, 14.3 mm and 35.1 mm, respectively. That is, the mean root lengths of the #878 strain were 34% greater after 8 days, 41% greater after 9 days and 33% greater after 12 days than the mean root lengths of the 1406 wild strain. In other words, the plant biomass of a plant having plant cells carrying the TaqI gene is increased even at an early stage (8 to 12 days after planting).

Example 5

(Inducing Endoreduplication by AtSIG2:TaqI-NLS Gene Introduction)

Figure 4:
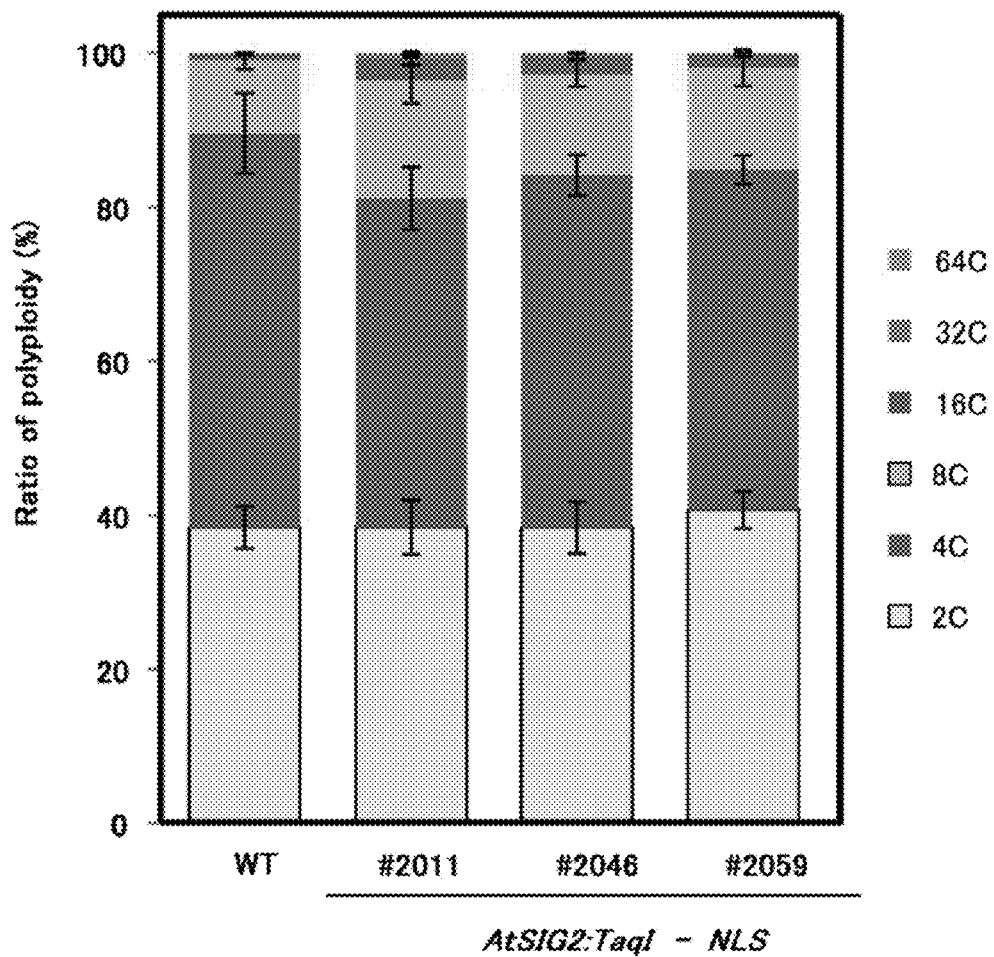
FIG. 4 shows ploidy level in an AtSIG2:TaqI-NLS transgenic strain.

After biomass quantity measurement, the first and second leaves were cut off rosettes of the #2011, #2046 and #2059 strains and the Col-0 wild strain, and subjected to nucleus extraction and genome DNA DAPI staining with a CyStain™ UV Precise P kit (Partec). Following genome DNA staining, the nuclei were subjected to flow cytometry with a Cell Lab Quanta SC MPL (Beckman Coulter) to measure the ploidy level of the leaf cells. The results are shown in FIG. 4. As shown in FIG. 4, the amount of 2C (diploidy) in the #2011, #2046 and #2059 strains was not much different than in the Col-0 wild strain. The amount of 4C (tetraploidy) was slightly lower in the #2011. #2046 and #2059 strains than in the Col-0 wild strain, but there was more 8C (octoploidy) and 16C (16-ploidy) in the #2011, #2046 and #2059 strains than in the Col-0 wild strain. The ploidy level of the #2011, #2046 and #2059 strains was higher than the ploidy level of the Col-0 strain. This shows that ploidy is increased in a plant having plant cells carrying the TaqI gene.

Figure 5:
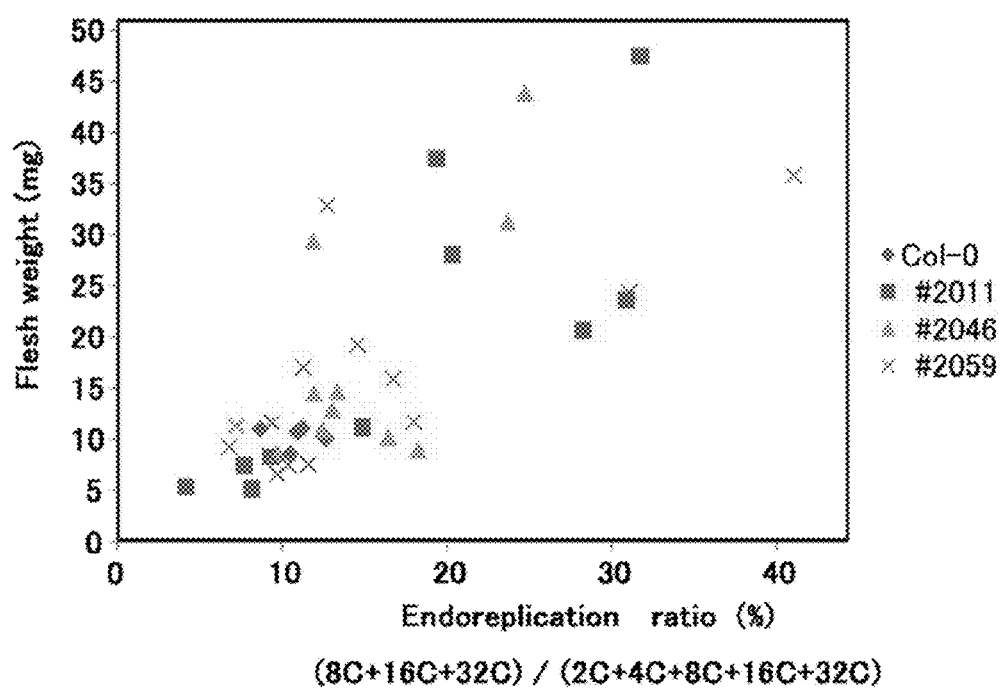
FIG. 5 shows correlation between endoreduplication ratio and biomass quantity in an AtSIG2:TaqI-NLS transgenic strain.

The correlation between biomass quantity and endoreduplication induction is shown in FIG. 5 for the #2011, #2046 and #2059 strains and the Col-0 wild strain. In FIG. 5, the endoreduplication ratio is used as an indicator of the degree of endoreduplication induction. The greater the endoreduplication ratio, the more endoreduplication has been induced.

Endoreduplication ratio=$(8C+16C+32C)/(2C+4C+8C+16C+32C)\times100$ (wherein 2C, 4C and other ploidy numbers represent the number of cells with that ploidy).

As shown in FIG. 5, the endoreduplication ratio correlates with biomass quantity for the #2011, #2046 and #2059 strains. That is, in a plant having plant cells carrying the TaqI gene, increased ploidy seems to result in increased biomass quantity.

Example 6

(Induction of Endoreduplication by 35S:TaqI-NLS Gene Introduction)

Figure 6:
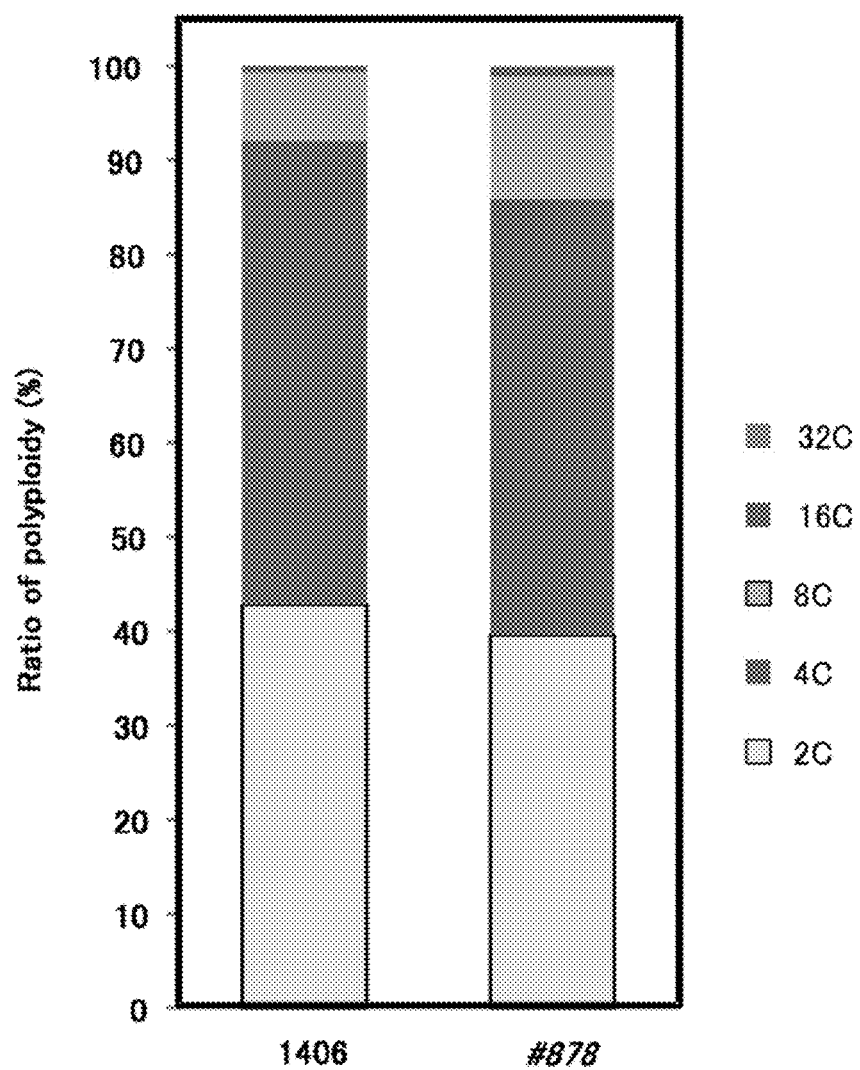
FIG. 6 shows ploidy level in a 35S:TaqI-NLS transgenic strain.

The leaf cell ploidy levels of the #878 strain and 1406 wild strain were measured by the same procedures used for the #2011, #2046 and #2059 strains and the Col-0 wild strain. The results are shown in FIG. 6. In FIG. 6, the amount of 2C and 4C is smaller in the #878 strain than in the 1406 wild strain. The amounts of 8C and 16C are greater in the #878 strain than in the 1406 wild strain. That is, the ploidy level of the #878 strain is greater than the ploidy level of the 1406 wild strain. This shows that ploidy is increased in a plant having plant cells carrying the TaqI gene.

Figure 7:
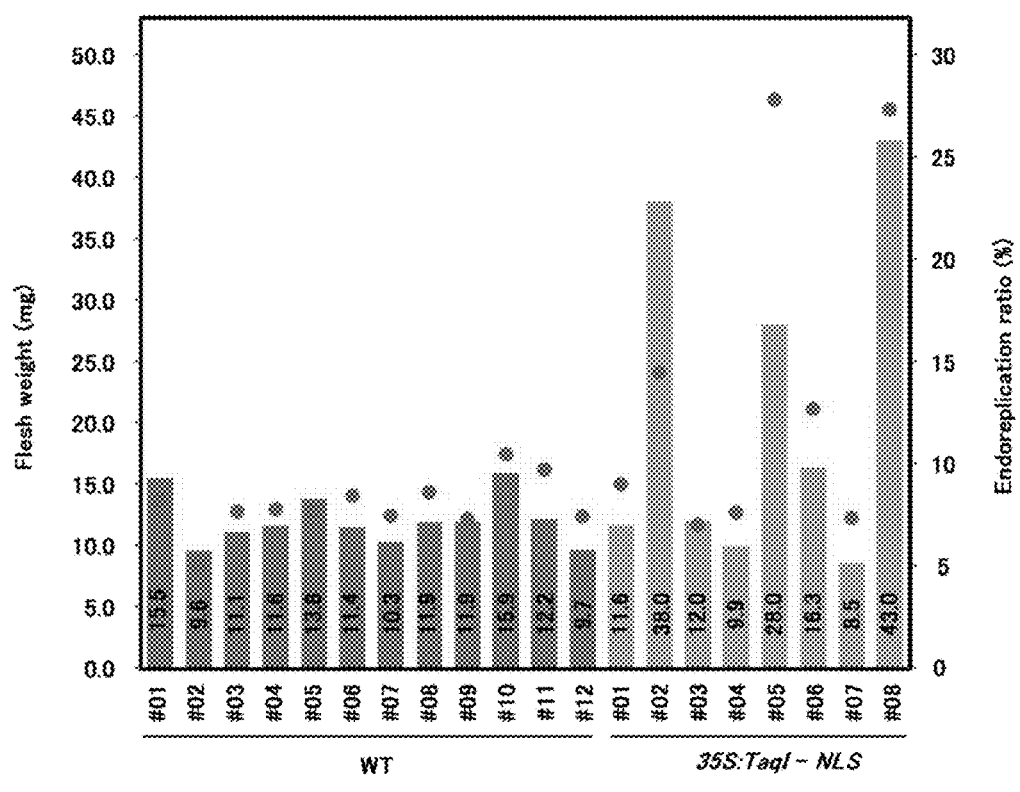
FIG. 7 shows endoreduplication ratio and biomass quantity in a 35S:TaqI-NLS transgenic strain.

FIG. 7 shows the biomass quantities and endoreduplication ratios of the #878 strain and 1406 wild strain. As shown in FIG. 7, individual plants of the #878 strain with large biomass quantities also had high endoreduplication ratios. This shows that increasing the ploidy results in an increase in biomass quantity in a plant having plant cells carrying the TaqI gene.

Example 7

(Gene Expression Analysis of 35S:TaqI-NLS Transgenic Strain)

Figure 8:
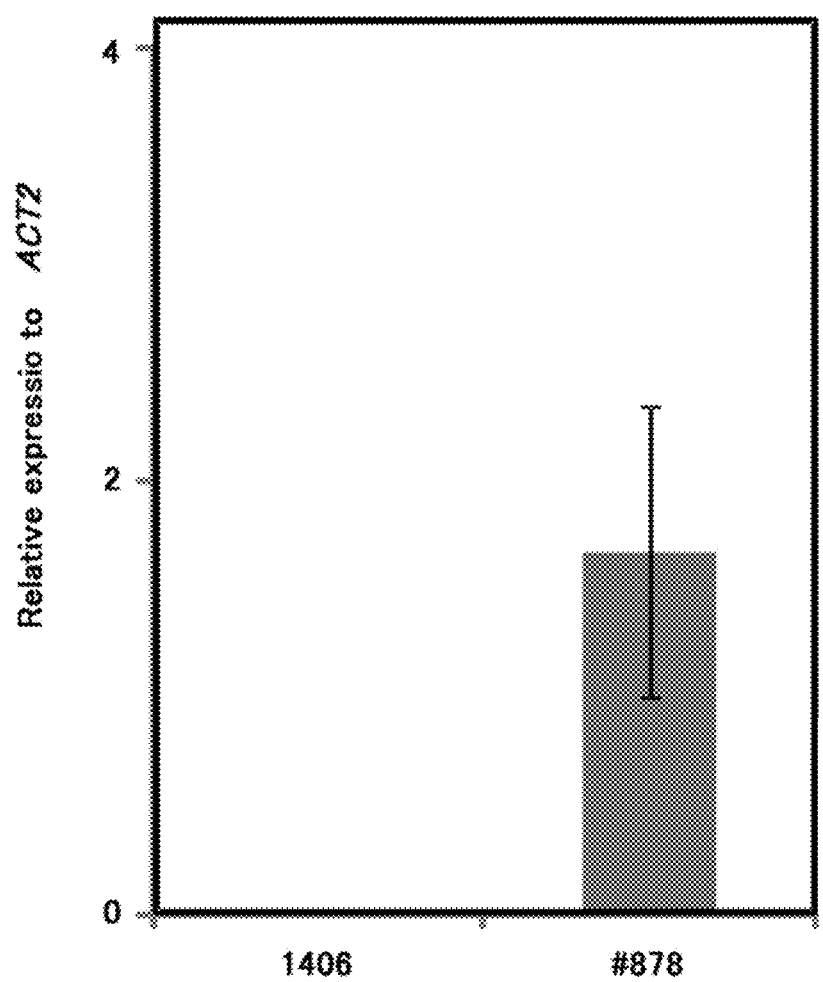
FIG. 8 shows the expressed amount of the TaqI gene in a 35S:TaqI-NLS transgenic strain.

Seeds of the aforementioned #878 strain having the TaqI-NLS gene inserted homozygously and seeds of the 1406 wild strain were planted in MS agar medium and grown for 2 weeks in a climate-controlled room at 22° C. with a light period of 16 hours, a dark period of 8 hours, and a light intensity of about 30 to 50 µmol/m²/sec, and total RNA was extracted with a RNeasy plant mini kit (Quiagen, Valencia, Calif.). Of the resulting RNA, the mRNA was assayed by quantitative real time PCR using a HIGH Capacity RNA-to-cDN™ Kit, a Power SYBR Green PCR Master Mix and an ABI PRISM 7000 (Lifetechnologies, Carlsbad, Calif.). The respective mRNA of the TaqI gene, RAD51 gene and AtACT2 gene was assayed using the primers shown below, and the expressed amount of the TaqI gene and the expressed amount of the RAD51 gene were determined as relative values relative to the expressed amount of the AtACT2 gene. As discussed above, the RAD51 coded for by the RAD51 gene is a protein that functions to repair DNA damage when double-stranded DNA is broken. FIG. 8 shows relative values for TaqI gene expression for the #878 strain and 1406 wild strain. It can be seen that while the TaqI gene was not expressed et all in the 1406 wild strain, the TaqI gene was expressed in the #878 strain. This confirms that the increased ploidy of the cells and the increased plant biomass are caused by TaqI gene expression.

```
                                    (SEQ ID NO: 10)
TaqI-F QRT: CATTGTCCGGACTCATACCC (SEQ ID NO: 11)
TaqI-R QRT: TTCTCTTCTCGTGGGCTTGT (SEQ ID NO: 12)
AtACT2-F RT: CTGTTGACTACGAGCAGGAGATGGA (SEQ ID NO: 13)
AtACT2-R RT: GACTTCTGGGCATCTGAATCTCTCA (SEQ ID NO: 14)
RAD51-R RT: CGAGGAAGGATCTCTTGCAG (SEQ ID NO: 15)
RAD51-R RT: GCACTAGTGAACCCCAGAGG
```

Figure 9:
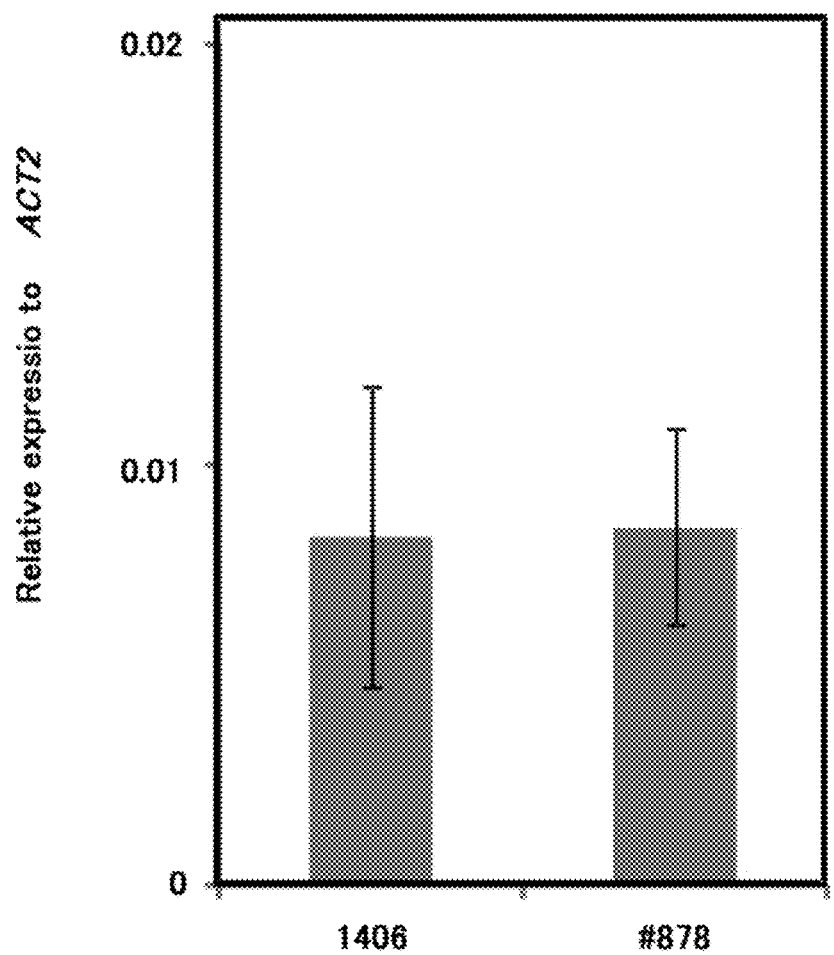
FIG. 9 shows the expressed amount of the RAD51 gene in a 35S:TaqI-NLS transgenic strain.

FIG. 9 shows relative values for RAD51 gene expression in the #878 strain and 1406 strain. As shown in FIG. 9, there was no significant difference in amount of expression of the RAD 51 gene between the #878 strain and the 1406 wild strain. As discussed above, the RAD51 gene is normally expressed when double-stranded DNA breakage occurs, but them was no increase in RAD51 gene expression in the #878 strain. This may be because the frequency of double-stranded DNA breakage was low in the #878 strain. Although the #878 strain carries the TaqI gene, DNA repair is not promoted because there is no increase in RAD51 gene expression. That is, the method of introducing the TaqI gene into plant cells is more suited to endoreduplication induction than other methods that increase the frequency of double-stranded DNA breakage.

[Sequence Table Free Text]
SEQ ID NOS:3 to 15: primers
[Sequence Tables]

What is claimed is:

1. A plant biomass production method, comprising:
 a. planting a plant having plant cells carrying an exogenous gene homozygously that encodes a TaqI restriction enzyme that promotes double-stranded DNA breakage, and
 b. growing the plant at least until after true leaf development, wherein
  expression of the exogenous gene that encodes the TaqI restriction enzyme in the plant cells in under control of a constant expression promoter, and
  the growing comprises growing the plant at a temperature that is lower than the optimum activation temperature of the TaqI restriction enzyme without transient activation of the TaqI restriction enzyme at the optimum activation temperature, so that the expressed amount of a RAD51 ortholog gene in the plant cells carrying the exogenous gene is less than two times the expressed amount in original plant cells that do not carry the exogenous gene, thereby increasing a mean biomass of the plant having the plant cells carrying the exogenous gene in comparison with a mean biomass of plants of a same species that do not carry the exogenous gene that are grown for a same amount of times as the plant having the plant cells carrying the exogenous gene.

2. The production method according to claim 1, wherein the expressed amount of a RAD51 ortholog gene in the plant cells carrying the exogenous gene is less than 1.5 times the expressed amount in the original plant cells that do not carry the exogenous gene.

3. The production method according to claim 1, wherein the expressed amount of the RAD51 ortholog gene in the plant cells carrying the exogenous gene is less than 1.2 times the expressed amount in the original plant cells.

4. The production method according to claim 1, wherein the growing further comprises growing the plant so that endoreduplication of the plant is induced, and a ration of endoreduplication of the plant is equal to or greater than 13%,
 wherein the ratio is evaluated by the following formula:

$$\text{Endoreduplication ratio} = (8C+16C+32C)/(2C+4C+8C+16C+32C) \times 100,$$

wherein 2C, 4C, 8C, 16C, and 32C represent the number of cells with that respective ploidy).

5. The production method according to claim 4, wherein the ratio of endoreduplication of the plant is equal to or grater than 15.0%.

6. The production method according to claim 4, wherein the ratio of endoreduplication of the plant is equal to or greater than 20.0%.

7. The production method according to claim 4, wherein the ratio of endoreduplication of the plant is equal to or greater than 30.0%.

8. The production method according to claim 1, wherein the constant expression promoter is selected from the group consisting of the cauliflower mosaic virus 35S promoter, *Arabidopsis thaliana* SIG2 promoter, rice actin promoter and corn ubiquitin promoter.

9. A plant biomass production method, comprising:
 a. planting a plant having plant cells homozygously carrying an exogenous gene that encodes a TaqI restriction enzyme that promotes double-stranded DNA breakage, and
 b. growing the plant at least until after true leaf development, wherein
  expression of the exogenous gene that encodes the TaqI restriction enzyme in the plant cells is under control of a constant expression promoter, and
  the growing comprises:
   growing the plant at a temperature that is lower than the optimum activation temperature of the TaqI restriction enzyme without transient activation of the TaqI restriction enzyme at the optimum activation temperature, so that the expressed amount of a RAD51 ortholog gene in the plant cells carrying the exogenous gene is less than two times the expressed amount in original plant cells that do not carry the exogenous gene, thereby increasing a mean biomass of plant having the plant cells carrying the exogenous gene in comparison with a mean biomass of plants of a same species that do not carry the exogenous gene that are grown for the same amount of time, and
   growing the plant so that endoreduplication of the plant is induced and a ration of endoreduplication of the plant is equal to or greater than 12.5%, wherein the ratio is evaluated by the following formula:

$$\text{Endoreduplication ratio} = (8C+16C+32C)/(2C+4C+8C+16C+32C) \times 100$$

wherein 2C, 4C, 8C, 16C, and 32C represent the number of cells with that respective ploidy.

* * * * *

```
                       SEQUENCE LISTING

<160> NUMBER OF SEQ ID NOS: 15

<210> SEQ ID NO 1
<211> LENGTH: 842
<212> TYPE: DNA
<213> ORGANISM: Arabidopsis thaliana

<400> SEQUENCE: 1 atggcccta cacaagccca gaaagtgctg gaagcttttg aggattttct gaagtgtttg      60
gacctcgaga gctaccaaga aaataccgc cccatcaaaa cagtagagca agacctacct     120
agagagctta acccacttcc agacttgtac gaccactatt ggaagcccaa cgggaacacc     180
cttcactttc cagattttga aactttcttc gaccagtggt gggagaagcg cctccggccc     240
ctaaacgagt ttattcgcaa gtattttgg ggatgttcct atgaatttgt ccgtctcggc      300
ttagaagcga ggctctaccg gaccgctgtt tccatttgga cgcaattca cttttcgtat      360 cgctggaacg cctcttgtca acttcgcttg acggccacct gggagttgga cgcccagggg     420
atagatgcac aaattcaagc agaagaccgc ctgataggca ttcagataaa aaggaaacc      480 tatcgctcgg aagcccggga gggaaaccgc ttcctaagaa ggcgcgaaca ttccgccctc     540
ctggaagttc cctacacgct gcaaagccca gaggaactcg aaagaaaagc ccagcgtgcc     600
cgaaccagag aagaagccta ccgcttgtgg gtcaaaatcg cccaccatct agaacggctt     660
cccaacggat tcgtcatctt ccgagaaagc tacgtaaagg acttggaaaa cttttttaaag    720 caaaacgcca ctacattgtc cggactcata ccctgggata aggtagcccg ggaagccctc     780
accggcccgt gaggtacacc cggaggacaa gcccacgaga agaagcccc cagggccacg      840 aa                                                                    842

<210> SEQ ID NO 2
<211> LENGTH: 263
<212> TYPE: PRT
<213> ORGANISM: Arabidopsis thaliana

<400> SEQUENCE: 2

Met Ala Pro Thr Gln Ala Gln Lys Val Leu Glu Ala Phe Glu Asp Phe
1               5                   10                  15

Leu Lys Cys Leu Asp Leu Glu Ser Tyr Gln Glu Lys Tyr Arg Pro Ile
            20                  25                  30

Lys Thr Val Glu Gln Asp Leu Pro Arg Glu Leu Asn Pro Leu Pro Asp
        35                  40                  45

Leu Tyr Asp His Tyr Trp Lys Pro Asn Gly Asn Thr Leu His Phe Pro
    50                  55                  60

Asp Phe Glu Thr Phe Phe Asp Gln Trp Trp Glu Lys Arg Leu Arg Pro
65                  70                  75                  80

Leu Asn Glu Phe Ile Arg Lys Tyr Phe Trp Gly Cys Ser Tyr Glu Phe
                85                  90                  95

Val Arg Leu Gly Leu Glu Ala Arg Leu Tyr Arg Thr Ala Val Ser Ile
            100                 105                 110

Trp Thr Gln Phe His Phe Cys Tyr Arg Trp Asn Ala Ser Cys Gln Leu
        115                 120                 125

Arg Leu Thr Ala Thr Trp Glu Leu Asp Ala Gln Gly Ile Asp Ala Gln
    130                 135                 140
```

-continued

Ile Gln Ala Glu Asp Arg Leu Ile Gly Ile Gln Ile Lys Lys Glu Thr
145                 150                 155                 160

Tyr Arg Ser Glu Ala Arg Glu Gly Asn Arg Phe Leu Arg Arg Arg Glu
                165                 170                 175

His Ser Ala Leu Leu Glu Val Pro Tyr Thr Leu Gln Ser Pro Glu Glu
            180                 185                 190

Leu Glu Arg Lys Ala Gln Arg Ala Arg Thr Arg Glu Glu Ala Tyr Arg
        195                 200                 205

Leu Trp Val Lys Ile Ala His His Leu Glu Arg Leu Pro Asn Gly Phe
    210                 215                 220

Val Ile Phe Arg Glu Ser Tyr Val Lys Asp Leu Glu Asn Phe Leu Lys
225                 230                 235                 240

Gln Asn Ala Thr Thr Leu Ser Gly Leu Ile Pro Trp Asp Lys Val Ala
                245                 250                 255

Arg Glu Ala Leu Thr Gly Pro
            260

<210> SEQ ID NO 3
<211> LENGTH: 45
<212> TYPE: DNA
<213> ORGANISM: Artificial
<220> FEATURE:
<223> OTHER INFORMATION: Synthetic Construct

<400> SEQUENCE: 3
aggatccccg ggtggtcagt cccttatggc ccctacacaa gccca         45

<210> SEQ ID NO 4
<211> LENGTH: 31
<212> TYPE: DNA
<213> ORGANISM: Artificial
<220> FEATURE:
<223> OTHER INFORMATION: Synthetic Construct

<400> SEQUENCE: 4
agagctctgt acctcacggg ccggtgaggg c         31

<210> SEQ ID NO 5
<211> LENGTH: 74
<212> TYPE: DNA
<213> ORGANISM: Artificial
<220> FEATURE:
<223> OTHER INFORMATION: Synthetic Construct

<400> SEQUENCE: 5
agagctcccc gggctatcct ccaacctttc tcttcttctt aggctgcaga cctcccgggc    60
cggtgagggc ttcc                                                     74

<210> SEQ ID NO 6
<211> LENGTH: 28
<212> TYPE: DNA
<213> ORGANISM: Artificial
<220> FEATURE:
<223> OTHER INFORMATION: Synthetic Construct

<400> SEQUENCE: 6
agtcgaccga tctttctcca acaagctt         28

<210> SEQ ID NO 7
<211> LENGTH: 29
<212> TYPE: DNA

```
<213> ORGANISM: Artificial
<220> FEATURE:
<223> OTHER INFORMATION: Synthetic Construct

<400> SEQUENCE: 7
aggatccgct cgttcttagc ctatattcg                                    29

<210> SEQ ID NO 8
<211> LENGTH: 40
<212> TYPE: DNA
<213> ORGANISM: Artificial
<220> FEATURE:
<223> OTHER INFORMATION: Synthetic Construct

<400> SEQUENCE: 8
agcttggcgc gccttaatta aactagtctc gaggtcgact                        40

<210> SEQ ID NO 9
<211> LENGTH: 40
<212> TYPE: DNA
<213> ORGANISM: Artificial
<220> FEATURE:
<223> OTHER INFORMATION: Synthetic Construct

<400> SEQUENCE: 9
ctagagtcga cctcgagact agtttaatta aggcgcgcca                        40

<210> SEQ ID NO 10
<211> LENGTH: 20
<212> TYPE: DNA
<213> ORGANISM: Artificial
<220> FEATURE:
<223> OTHER INFORMATION: Synthetic Construct

<400> SEQUENCE: 10
cattgtccgg actcataccc                                              20

<210> SEQ ID NO 11
<211> LENGTH: 20
<212> TYPE: DNA
<213> ORGANISM: Artificial
<220> FEATURE:
<223> OTHER INFORMATION: Synthetic Construct

<400> SEQUENCE: 11
ttctcttctc gtgggcttgt                                              20

<210> SEQ ID NO 12
<211> LENGTH: 25
<212> TYPE: DNA
<213> ORGANISM: Artificial
<220> FEATURE:
<223> OTHER INFORMATION: Synthetic Construct

<400> SEQUENCE: 12
ctgttgacta cgagcaggag atgga                                        25

<210> SEQ ID NO 13
<211> LENGTH: 25
<212> TYPE: DNA
<213> ORGANISM: Artificial
<220> FEATURE:
<223> OTHER INFORMATION: Synthetic Construct

<400> SEQUENCE: 13
gacttctggg catctgaatc tctca                                        25
```

```
<210> SEQ ID NO 14
<211> LENGTH: 20
<212> TYPE: DNA
<213> ORGANISM: Artificial
<220> FEATURE:
<223> OTHER INFORMATION: Synthetic Construct

<400> SEQUENCE: 14
cgaggaagga tctcttgcag                                              20

<210> SEQ ID NO 15
<211> LENGTH: 20
<212> TYPE: DNA
<213> ORGANISM: Artificial
<220> FEATURE:
<223> OTHER INFORMATION: Synthetic Construct

<400> SEQUENCE: 15
gcactagtga accccagagg                                              20
```